United States Patent
Akita et al.

(10) Patent No.: US 6,475,767 B1
(45) Date of Patent: Nov. 5, 2002

(54) PROCESS FOR PRODUCING L-METHIONINE γ-LYASE CRYSTALS

(75) Inventors: Kensaku Akita, Hyogo; Tomoaki Takakura, Nara; Akio Takimoto, Hyogo; Takaomi Ito, Osaka, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/367,974

(22) PCT Filed: Mar. 11, 1998

(86) PCT No.: PCT/JP98/00993

§ 371 (c)(1),
(2), (4) Date: Aug. 24, 1999

(87) PCT Pub. No.: WO98/40476

PCT Pub. Date: Sep. 17, 1998

(30) Foreign Application Priority Data

Mar. 13, 1997 (JP) ............................................. 9-059177
Oct. 3, 1997 (JP) ............................................. 9-270676

(51) Int. Cl.⁷ ............................. C12N 9/88; C12N 1/20; C12N 15/00; C12P 21/06; C07H 21/04
(52) U.S. Cl. ................... 435/232; 435/69.1; 435/252.3; 435/320.1; 424/94.5; 536/23.2
(58) Field of Search ................................ 435/232, 69.1, 435/252.3, 320.1; 424/94.5; 536/23.2

(56) References Cited

U.S. PATENT DOCUMENTS 5,120,650 A * 6/1992 Visuri ......................... 435/176

FOREIGN PATENT DOCUMENTS

| WO | WO9411535 A1 | 5/1994 |
| WO | WO 96-40284 | 12/1996 |
| WO | WO 99/07858 | 2/1999 |

OTHER PUBLICATIONS

Nakayama et al., *Analytical Biochemistry*, vol. 138, pp. 421–424 (1984).
Inoue et al., *J. Biochem.*, vol. 117, pp. 1120–1125 (1995).
Lishko et al., *Protein Expression and Purification*, vol. 4, pp. 529–533 (1993).
Esaki et al., *Methods in Enzymology*, vol. 143, pp. 459–465 (1987).
Nobuyoshi Esaki et al, Methods in Enzymology (1987), vol. 143, pp. 459–465.
Hiroyuki Inoue et al, J. Biochem. (1995), vol. 117, No. 5, pp. 1120–1125.
Tan Y. et al., "Polyethylene glycol conjugation of recombinant methioninase for cancer therapy." US National Library Of Medicine, Feb. 1998, 12(1), pp. 45–52, XP 002182531.

* cited by examiner

*Primary Examiner*—Tekchand Seidha
(74) *Attorney, Agent, or Firm*—Birch, Stewart, Kolasch & Birch, LLP (57) ABSTRACT

A process for production of L-methionine γ-lyase crystals by using polyethylene glycol, characterized by comprising the first step of warming a solution containing L-methionine γ-lyase before or after addition of polyethylene glycol thereto and the second step of adding an inorganic salt.

20 Claims, 5 Drawing Sheets

PROCESS FOR PRODUCING L-METHIONINE γ-LYASE CRYSTALS

This application is the national phase under 35 U.S.C. §371 of PCT International Application No. PCT/JP98/00993 which has an International filing date of Mar. 11, 1998 which designated the United States of America.

TECHNICAL FIELD

This invention relates to a process for production of crystals of L-methionine γ-lyase useful as an antitumor agent, a process for purification of L-methionine γ-lyase comprising the process for production of crystals and recombinant L-methionine γ-lyase crystals producable by the process for this producing system.

BACKGROUND ART

L-Methionine γ-lyase (EC 4.4.1.11) is an enzyme which requires pyridoxal phosphate as a coenzyme and catalyzes α,γ-elimination and γ-replacement of L-methionine or its derivatives and also α,β-elimination and β-replacement of S-substituted L-cysteine or its derivatives. It was reported that the enzyme was isolated and purified from *Pseudomonas putida* (Nakayama, T. et al., Anal. Biochem. 138, 421–424 (1984)). Recently, it was found that L-methionine γ-lyase has an antitumor activity (WO94/11535). In the past, L-methionine γ-lyase could be obtained in very small quantity from *Pseudomonas. putida*. However, recent development of recombinant DNA technology provides a possibility of its large quantity production (Inoue, H. et al., J. Biochem. 117, 1120–1125 (1995)).

Needless to say, a drug used as a pharmaceutical preparation should be pure. In the past, L-methionine γ-lyase was extracted from cells of *Pseudomonas putida* and purified by a combination of ion-exchange column chromatographies (Nakayama, T. et al., Anal. Biochem. 138, 421–424 (1984), Lishko, V K et al., Protein expression and purification 4, 529–533 (1993)). However, such enzyme did not have an enough purity to be used as pharmaceutical preparations, and it was difficult to purify it on a large scale.

As a method for production of protein crystals, a method using polyethylene glycol is well known. Concerning L-methionine γ-lyase, a procedure of its crystallization was reported (Esaki, N. et al., Methods in Enzymol. 143, 459–465 (1987)). The crystallization was performed by mixing L-methionine γ-lyase with a potassium phosphate buffer containing polyethylene glycol and leaving the mixture at room temperature (so called vapor diffusion method). In the paper, however, L-methionine γ-lyase of high purity which had previously been purified by column chromatographies was used for the crystallization. Moreover, the quantity of the crystals obtained was very small (1.6 mg).

DISCLOSURE OF INVENTION

It is difficult to produce a large quantity of crystals from a protein which has not been purified and contains impurities. Even though such crystallization succeeded, it was often impractical because the crystals still contain impurities. Therefore, a large scale crystallization at such step has hardly been attempted. This invention aims to provide a process for production of a large quantity of pure L-methionine γ-lyase crystals from unpurified L-methionine γ-lyase, and a process for purification of L-methionine γ-lyase which comprises the process for production.

From the result of intensive studies for the above purpose, the present inventors have found out that a highly purified L-methionine γ-lyase crystals can be produced in a short time by the method for production of L-methionine γ-lyase crystals using polyethylene glycol, that is to say, the first step is the warming of a solution containing L-methionine γ-lyase before or after addition of polyethylene glycol thereto and the second step is the addition of an inorganic salt. Thus, the present invention has been accomplished.

In this invention, L-methionine γ-lyase means either or both of a natural L-methionine γ-lyase produced by a microorganism such as *Pseudomonas putida* and a recombinant L-methionine γ-lyase prepared by a recombinant DNA technique. From the point of view for industrial mass production, the recombinant L-methionine γ-lyase is preferred. Therefore, though the recombinant L-methionine γ-lyase (hereinafter referred to as "rMETase") is used for explanations in the embodiments of the present invention, the natural L-methionine γ-lyase can also been used.

A solution containing L-methionine γ-lyase used in the process for producing the crystals of the invention means any of solutions which contain unpurified or purified L-methionine γ-lyase. Examples of the solution include a crude enzyme solution described in the following step 1, a solution containing unpurified L-methionine γ-lyase and a solution obtained after eliminating impurities by using polyethylene glycol. However, these examples do not limit the scope of this invention.

Additionally, cationic high molecular coagulants are used for eliminating nucleic acids or endotoxins as insoluble agglutinates by binding the cationic groups to anion groups of nucleic acids or endotoxins. Examples of the coagulants include polyethyleneimine or a cationic high molecular coagulant which mainly consists of chitosan (preferred is Kurimover I (Kurita Water Industries Ltd, Tokyo, Japan)). However, these examples do not limit the scope of this invention.

BEST MODE FOR CARRYING OUT THE INVENTION

1. Preparation of Solution Containing L-methionine γ-lyase (rMETase)

(1) Cultivation of rMETase Expression Strain

An expression plasmid, into which a structural gene of L-methionine γ-lyase is inserted, is prepared according to the method described in Inoue, H. et al., J. Biochem. 117, 1120–1125 (1995). More concretely, the expression plasmid is prepared by inserting a DNA fragment containing L-methionine γ-lyase gene into pKK223-3, pPL-Lambda or other vectors which have a suitable promoter for effective expression of rMETase gene in a *E.coli* such as lac, tac, trp, trc, or λ PL and Shine-Dalgarno (SD) sequence or into pKK233-2, pTrc99A or other ATG vectors which have a translation initiation codon ATG The expression plasmid is introduced into a suitable host cell such as *E.coli* strains HB101, JM103, JM105, JM109, C600, MV1184, DH1, DH5, DH5, α, BL21. Thus, a rMETase expression strain is obtained and cultured.

(2) Elimination of the Cell Debris

After the cultivation, the cells are disrupted by a high pressure homogenizer (APV-Gaulin) at 20 to 55° C., preferably at about 42° C. A cationic high molecular coagulant is added to it. As the cationic high molecular coagulant, polyethyleneimine or Kurimover I is given for example. After adjusting the final concentration of the cationic high molecular coagulant to 0.05–0.5% (w/v), preferably 0.1–0.2% (w/v), the cell debris is eliminated by the cationic high molecular coagulant at 5 to 25° C. for 1 to 20 minutes to obtain a solution of crude rMETase. Instead of the elimination by the cationic high molecular coagulant, the cell debris can be eliminated by cell disruption using a high pressure homogenizer, centrifugation, and heat treatment of the supernatant at 55 to 65° C. for 1 to 10 minutes. The obtained crude enzyme solution is salted out by an ammonium sulfate and centrifuged. The obtained precipitates are dissolved in a buffer solution, preferably a phosphate buffer solution, to obtain a solution containing unpurified L-methionine γ-lyase (rMETase).

(3) Elimination of Impurities

Subsequently, polyethylene glycol of which final concentration is from 5 to 25% (W/V), preferably from about 8 to about 12% (W/V) is added to the unpurified rMETase-containing solution. The mixture is stirred at about 2° C. to about 15° C., preferably 4° C. for about 10 minutes to about 120 minutes, preferably about 60 minutes and centrifuged to eliminate impurities. As the polyethylene glycol, it is preferred that its average molecular weight is not less than about 7,200 (eg, PEG 6000). By addition at this step of ammonium sulfate to make its final concentration 8 to 10%, preferably 10% as a saturation concentration, the solubility of rMETase becomes higher and the loss of rMETase can be minimized.

2. Production of rMETase Crystals (1) The L-methionine γ-lyase-containing solution, preferably the solution from which impurities are eliminated at the above described step 1, is warmed and polyethylene glycol is added. The warming can be performed either before or after the addition of polyethylene glycol. The polyethylene glycol can be added before and/or after the warming. In this case, the addition of polyethylene glycol before the warming may be done for the above described purpose of eliminating impurities.

The temperature after the warming is about 25° C. to about 40° C., preferably about 30° C. to about 32° C. In general, crystallization is promoted by refrigeration. In this invention, the crystallization of L-methionine γ-lyase was unexpectedly promoted by warming at this stage. This is one of the most important points of this invention.

The addition of polyethylene glycol can be performed according to usual methods for protein crystallization. In preferred embodiment, polyethylene glycol having the molecular weight not less than about 7,200 is added to make its final concentration about 5 to about 25% (W/V), followed by mixing and dissolving. In the case that polyethylene glycol is separately added before and after the warming, the total concentration of polyethylene glycol should be adjusted to the final concentration mentioned above. In the case that the rMETase containing-solution prepared in the step 1 is used, polyethylene glycol may be added to reach the above described final concentration including the remained polyethylene glycol which has been added for elimination of impurities (2) Further, an inorganic salt is added to give prismatic crystals of rMETase. As the inorganic salt, alkaline metal salts such as sodium chloride and potassium chloride are given for example. Especially, sodium chloride is preferred. The inorganic salt is used preferably at the final concentration of about 20 mM to about 500 mM, more preferably at about 100 mM to about 200 mM. The inorganic salt is added in 10 minutes to two hours, preferably in 20 minutes.

The crystals can be formed from the solution without mixing. However, it is preferred to mix the solution during the above described steps (1) and (2). The solution for the crystallization is preferably maintained at pH 7 to 8, more preferably at 7.2 to 7.5.

The crystals of rMETase can be separated by centrifugation.

The obtained rMETase crystals are of high purity and pyrogenic substance has been decreased. The crystals could be stored under cool condition in long term period.

Highly purified rMETase crystals containing extremely little contaminant proteins can be obtained by repeating the steps (1) and (2). The rMETase obtained by this crystallization has the same or higher purity than that obtained by combination of several column chromatographies without crystallization. Further, purification after the crystallization of this invention (e.g., column chromatography such as ion-exchange column chromatography and size exclusion column chromatography) provides highly purified rMETase crystals, in which the amount of other contained proteins is very little and the concentration of pyrogenic substance is controlled to a low level enough to obtain a permission of pharmaceutical use, the marketing approval as drugs.

It is obvious that the crystallization method has industrial and economical advantages against chromatography method. Therefore, the method of purification of L-methionine γ-lyase which includes the process for producing the crystals of this invention is very useful for industrial use.

Recombinant L-methionine γ-lyase crystals which are produced by the producing process of this invention are novel. This invention also provides these novel crystals. The rMETase crystals produced according to this invention had the same enzymatic activity as that of the natural protein and the amino acid sequences were identical to each other.

This invention is explained in more detail by showing examples and reference examples which do not limit the scope of this invention.

REFERENCE EXAMPLE 1

Cultivation of rMETase Expression Strain rMETase expression plasmid pYH301 (Inoue, H. et al, J. Biochem, 117, 1120–1125 (1995)) was constructed by inserting a L-methionine γ-lyase structural gene into expression vector pKK223-3 (Amersham Pharmacia Biotech). This plasmid was introduced into *Escherichia coli* JM109 to be used as a rMETase expression strain. After incubation in LB medium as seed culture, the cells were cultured for 24 hours at 37° C. in Terrific broth (Funakoshi, Tokyo, Japan).

REFERENCE EXAMPLE 2

Preparation of Crude Enzyme Solution 300 ml of a culture broth obtained in Reference example 1 was centrifuged. About 20 g of wet cells were collected and suspended in 140 ml of a buffer solution for cell disruption (1.3 mM pyridoxal phosphate (PLP), 0.01% dithiothreitol (DTT), 100 mM sodium phosphate buffer solution (Na-PB), pH 7.2), then disrupted. The suspension after the cell disruption was centrifuged, and 146 ml of cell extract was obtained (specific activity of rMETase:20 U/mg). The cell extract was heated at 60° C. for 5 minutes, cooled, and centrifuged again to give 136 ml of clear lysate as a crude enzyme solution (specific activity of rMETase:30 U/mg). Otherwise, 155 ml of the suspension after the cell disruption was treated with polyethyleneimine at 10° C. for 5 minutes and centrifuged to give 136 ml of clear lysate as a crude enzyme solution (specific activity of rMETase:20 U/mg).

REFERENCE EXAMPLE 3

Assay of rMETase Activity

The activity of rMETase was determined as follows. The rMETase solution obtained in the above Reference examples was diluted with a dilution buffer (10 µM PLP, 1 mM EDTA.2Na.2H$_2$O, 0.1 g/l (±)-dithiothreitol, 0.5 g/l Tween 80, 100 mM potassium phosphate buffer solution (K-PB, pH8.0)) to prepare a dilution enzyme solution. A solution containing L-methionine as a substrate was preincubated at 37° C. for 5 minutes (25mM L-methionine, 10 µM PLP, 100 mM K-PB (pH 8.0)), to which 50 µl of the dilution enzyme solution was added, and the mixture was reacted at 37° C. for 10 minutes. 100 µl of trichloroacetic acid (500 g/L) solution (hereinafter referred to as TCA solution) was added to terminate the enzyme reaction. The mixture of 0.8 ml of the obtained enzyme reaction solution, 1.6 ml of an acetic acid buffer solution (1 M sodium acetate/acetic acid, pH 5.0) and 0.60 ml of MBTH solution (1 g/L 3-methyl-2-benzothiazolinone hydrazone HCl.H$_2$O) was reacted at 50° C. for 30 minutes, then cooled to room temperature. The amount of produced α ketobutyrate was determined by measuring the absorbance at 320 nm ($E_{320}$ sample). The reference absorbance was similarly determined as a blank ($E_{320}$ blank) by adding the dilution enzyme solution and TCA solution vice versa. 1 Unit (U) of the enzyme was defined as the amount of the enzyme producing 1 µmol of α ketobutyrate for 1 minute.

Enzyme activity(U/ml)=(1.15·3.00/15.74/0.05/0.80/10)·($\Delta E$+2($\Delta E$)$^2$)=0.5480·($\Delta E$+2($\Delta E$)$^2$)

Where, $\Delta E$: $E_{320}$sample−$E_{320}$blank, 1.15: Quantity of enzyme reaction solution (ml), 3.00 Quantity of MBTH reaction solution (ml), 15.74: molecular extinction coefficient of azine derivatives (mM), 0.05: Quantity of enzyme reaction sample solution (ml), 0.80: Quantity of MBTH reaction sample solution (ml), 10: Reaction time (minute))

REFERENCE EXAMPLE 4

Purification of rMETase By Column Chromatography

A crude enzyme solution was obtained by cell disruption and heat treatment according to Reference example 2. 270 ml of deioninzed water which contained 10 µM PLP and 0.01% 2-mercaptoethanol (2-ME) was added to 136 ml of the crude enzyme solution. The crude enzyme solution was adjusted to be pH 7.2 and applied to 100 ml DEAE-TOYOPEARL 650C column (Tosoh Corp., Tokyo, Japan) which had been equilibrated with 10 mM Na-PB (pH 7.2). The column was washed with 10 mM Na-PB (pH 7.2) which contained 50 mM NaCl, 10 µM PLP and 0.01% 2-ME. The enzyme was eluted with 10 mM Na-PB (pH 7.2) which contained 100 mM NaCl, 10 µM PLP and 0.01% 2-ME. The specific activity of the rMETase was about 46 U/mg. 100 ml of 10 mM Na-PB (pH 8.0) which contained 10 µM PLP and 0.01% 2-ME was added to about 100 ml of the obtained active fraction, and the mixture was adjusted to be pH 8.0 and applied to 50 ml DEAE-Sepharose FF column (Amersham Pharmacia Biotech) which had been equilibrated with 50 mM Na-PB (pH 8.0). The column was washed with 50 mM Na-PB (pH 8.0) which contained 80 mM NaCl, 10 µM PLP and 0.01% 2-ME. The enzyme was eluted with 50 mM Na-PB (pH 8.0) which contained 120 mM NaCl, 10 µM PLP and 0.01% 2-ME. The specific activity of the rMETase was about 50 U/mg. The obtained active fraction was concentrated by a membrane which has a cutting size of 100 kDa (Millipore). 10 ml of the concentrated solution was applied to 400 ml Sephacryl S-200 HR column (Pharmacia Biotech) which had been equilibrated with 10mM Na-PB (pH 7.2) contained 10 mM PLP. The specific activity of the obtained effective active fraction of the rMETase was 52 U/mg. The specific activity and yield of rMETase obtained after each purification step were shown in Table 1.

TABLE 1

| Purification Steps | Specific Activity (U/mg) | Yield (%) |
| --- | --- | --- |
| Supernatant after cell disruption | 20 | 100 |
| Crude enzyme solution | 30 | 85 |
| DEAE-TOYOPEARL | 46 | 65 |
| DEAE-Sepharose FF | 50 | 50 |
| Concentrated Solution | 50 | 48 |
| Sephacryl S-200 HR | 52 | 40 |

Example 1

Preparation of rMETase Crystals—(1)

Figure 1:
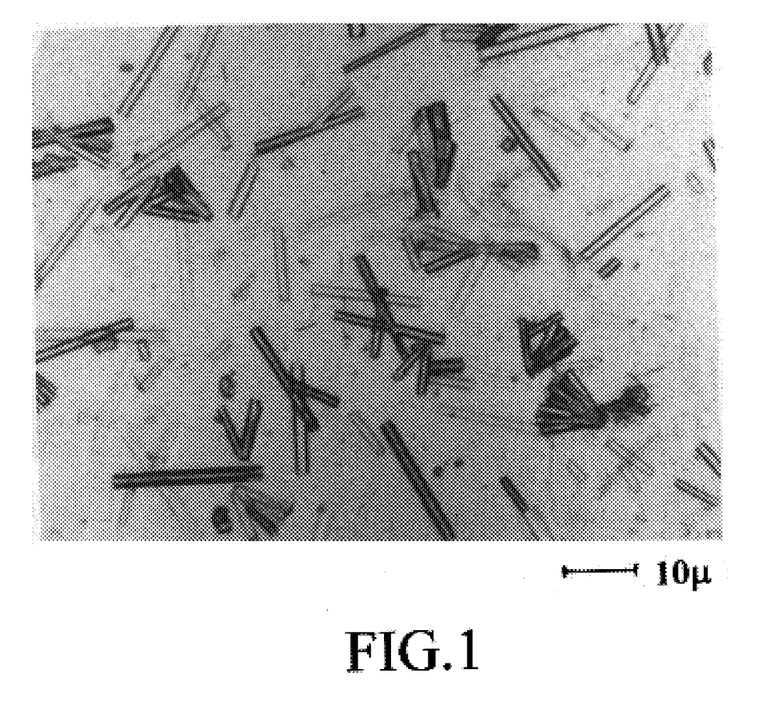
FIG. 1 is a picture showing prismatic crystals of rMETase.

58 g of solid ammonium sulfate (65% saturation) was added gradually to 136 ml of the crude enzyme solution prepared according to Reference example 2. The solution was adjusted by aqueous ammonia to be pH 7.2 during addition of ammonium sulfate. The enzyme was salted out from the solution. The precipitates were collected by centrifugation and stored in a refrigerator. The precipitates were dissolved in 40 ml of a dissolution buffer (500 µM PLP, 0.05% 2-ME and 100 mM Na-PB, pH7.2) and 4 g of PEG 6,000 (10% (W/V)) was added gradually, then the mixture was stirred at 4° C. for 60 minutes. After eliminating insoluble substances by centrifugation, the solution was stirred at 4° C. for 16 hours. The resultant solution was warmed to 30° C. and 0.8 g of PEG 6,000 (2% (w/v)) was added thereto with stirring to dissolve the PEG 6,000. 2 ml of 4 M NaCl solution was added to the solution with stirring. The mixture was further stirred at 30° C. for 60 minutes to produce prismatic crystals. After further stirring at 4° C. for 20 hours, the prismatic crystals of rMETase were obtained by centrifugation (FIG. 1).

Example 2

Preparation of rMETase Crystals—(2)

Figure 2:
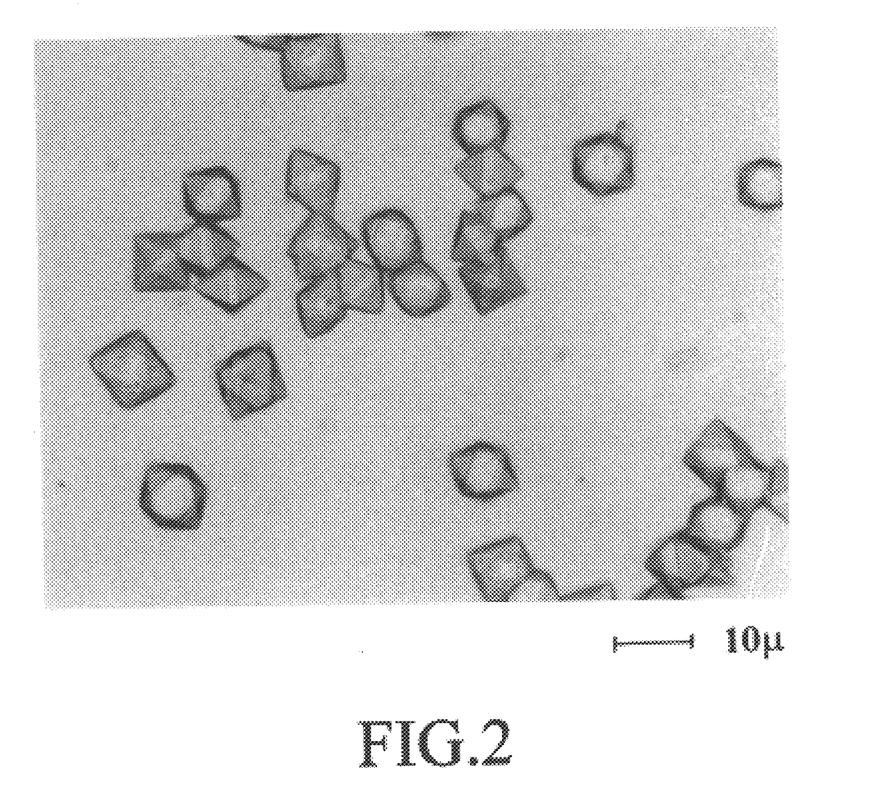
FIG. 2 is a picture showing bi-pyramidal crystals of rMETase.

The prismatic crystals obtained at above Example 1 were dissolved in 40 ml of a dissolution buffer. This solution was warmed at 30° C. and 4 g of PEG 6,000 (10% (W/V)) was added to the solution little by little with stirring to dissolve. 2 ml of 4 M NaCl solution was added to the solution and the mixture was stirred at 4° C. for 20 hours. Appeared bi-pyramidal crystals were collected by centrifugation. These crystals were dissolved in 35 ml of the dissolution buffer. After warming the solution to 30° C., 3.5 g of PEG 6,000 (10% (W/V)) was added thereto with stirring to dissolve. 1.75 ml of 4 M NaCl solution was added with stirring and the mixture was further stirred at 4° C. for 20 hours. The bi-pyramidal crystals were collected by centrifugation (FIG. 2).

These crystals which were obtained in the above Examples 1 and 2 were highly purified to show a single band by SDS polyacrylamide gel electrophoresis. It was confirmed that crystallization of this invention showed a high purification effect. Further, such obtained specific activity, purity and yield were same or higher than those of the rMETase which obtained by the purification method combined with ion-exchange column chromatographies mentioned in the above Reference example 4.

Example 3
Application of rMETase Crystals to Column Chromatography

The crystals obtained in example 2 were dissolved in 60 ml of the dissolution buffer. The solution was applied to 50 ml of DEAE-Sepharose FF (Amersham Pharmacia Biotech) column chromatography which had been equilibrated with 20 mM Na-PB (pH 7.2). The column was washed with 20 mM Na-PB (pH 7.2) which contained 50 mM NaCl, 10 μM PLP and 0.01% 2-ME. The enzyme was eluted with 20 mM Na-PB (pH 7.2) which contained 100 mM NaCl, 10 μM PLP and 0.01% 2-ME. The specific activity of the rMETase was about 52 U/mg. The obtained active fraction was concentrated to be 10 ml by a membrane which has a cutting size of 100 kDa (Millipore). 10 ml of the concentrated solution was applied to 400 ml of Sephacryl S-200 HR (Pharmacia Biotech) column chromatography which had been equilibrated with 10 mM Na-PB (pH 7.2) containing 10 μM PLP. The specific activity of the obtained effective active fraction of the rMETase was 52 U/mg.

The specific activity and yield of rMETase obtained after each operation in Examples 1 to 3 were shown in Table 2.

TABLE 2

|  | Purification Step | Heat Treatment | | Polyethyleneimine Treatment | |
|---|---|---|---|---|---|
|  |  | Sp. act. (U/mg) | Yield (%) | Sp. act. (U/mg) | Yield (%) |
| Example 1 | Supernatant after cell disruption | 20 | 100 | 20 | 100 |
|  | Crude enzyme solution | 30 | 85 | 20 | 92 |
|  | Unpurified rMETase solution | 34 | 78 | 28 | 85 |
|  | rMETase prismatic crystals | 52 | 70 | 52 | 77 |
| Example 2 | rMETase bi-pyramidal crystals | 52 | 65 | 52 | 72 |
| Example 3 | DEAE-Sepharose FF | 52 | 55 | 52 | 61 |
|  | Concentrated solution | 52 | 53 | 52 | 59 |
|  | Sephacryl S-200 HR | 52 | 48 | 52 | 53 |

Sp. act.: Specific Activity

Example 4
Preparation of Novel Expression Plasmid

The rMETase gene from which the initiation codon was excluded (rMETase (-ATG)) was cloned by a PCR method using pYH301 containing rMETase gene as a template. 1 μl of 10 pmol sense primer (SEQ ID No.1: 5'-CCCGGTACCA CGGCTCCAAC AAGCTCCCAG-3'), 1 μl of 10 pmol antisense primer (SEQ ID No.2:5'-CTCGAGACGG GTTCAGGCAC TCGCCTT-3'), and 8 μl of dNTP (each 2.5 mM) and a tablet of Ampli Wax™ (Perkin-Elmer Corp., Conn., USA) were mixed and the resulting mixture was heated at 77° C. for 7 minutes, then cooled at 20° C. for 3 minutes. 0.5 μl of 5 U/ml Taq DNA polymerase (Takara Shuzo Co., Kyoto, Japan) and about 1 μl of 1 mg/ml pYH301 were added and the quantity of the solution was filled up to 90 μl with distilled water, then 10 μl of PCR amplification buffer which is attached to the Polymerase Kit was added.

PCR amplification was conducted with DNA Thermal Cycler (Model PJ2000:Perkin-Elmer Corp.). The reaction was set up as 1 minute at 94° C., 1.5 minutes at 55° C., and 2 minutes at 72° C. per cycle and performed 20 cycles. The resultant mixture was heated at 72° C. for 7 minutes and placed at room temperature. The whole quantity of an aqua phase under a solidified wax layer was electrophoresed on agarose gel. The amplified fragments were recovered by a DNA recovering System SpinBindm™ (Takara Shuzo Co.) 2 μl of the collected DNA fragments, 1 μl of pMOSBlue T-vector (Amersham Pharmacia Biotech) and 17 μl of distilled water were added to Ready-To-Go™ T4 DNA ligation kit (Amersham Pharmacia Biotech) and the mixture was incubated at 16° C. for 45 minutes, and then E.coli DH5 strain was transformed. The transformant was incubated on an agar medium containing ampicillin. A plasmid containing a rMETase gene and an ampicillin resistant gene which were inserted in opposite direction was selected from the transformants and named as LMGL/T-vector.

Figure 3A:
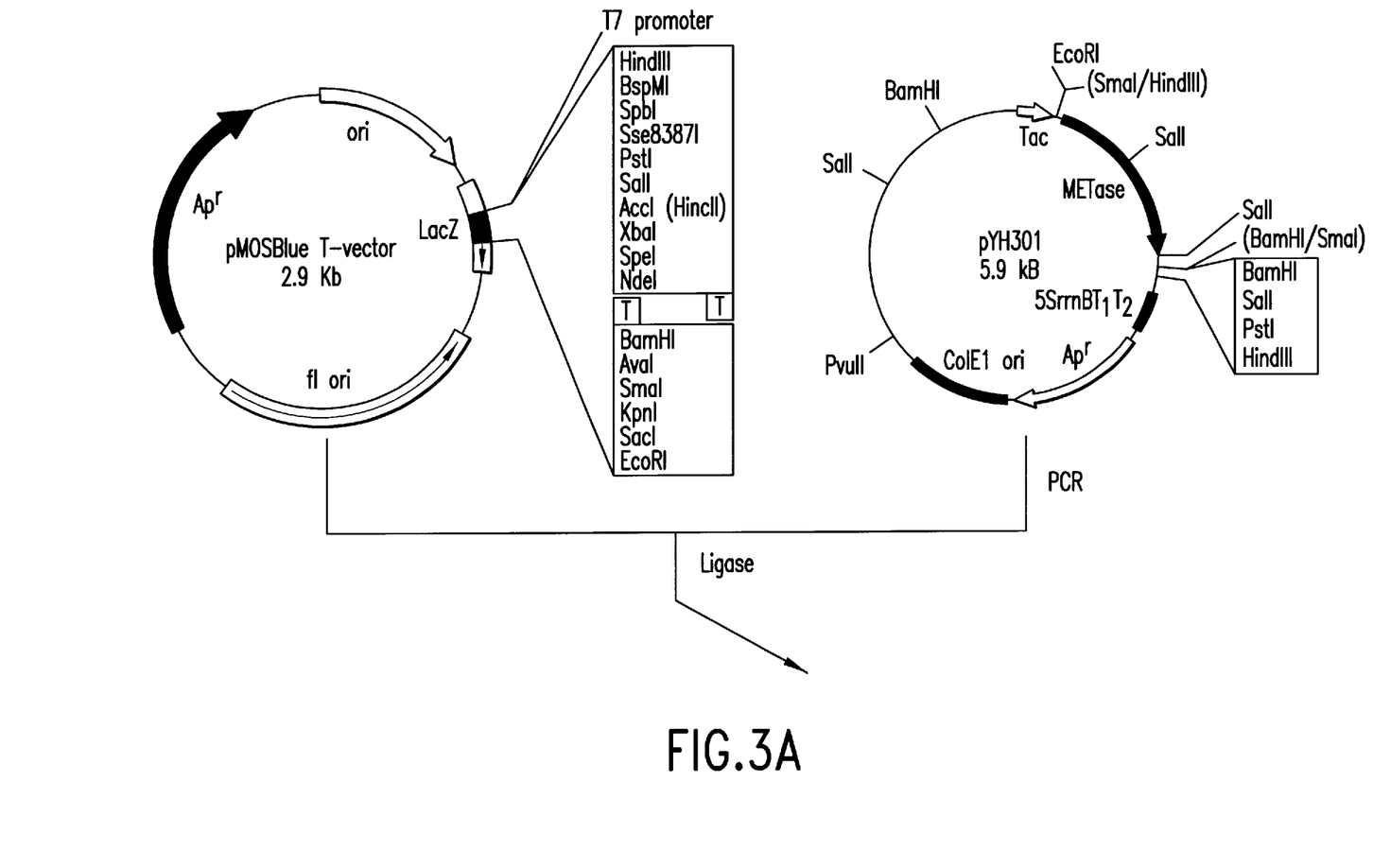
FIG. 3 is a drawing of a strategy for preparing a novel rMETase expression plasmid pMGLTrc03.
Figure 3B:
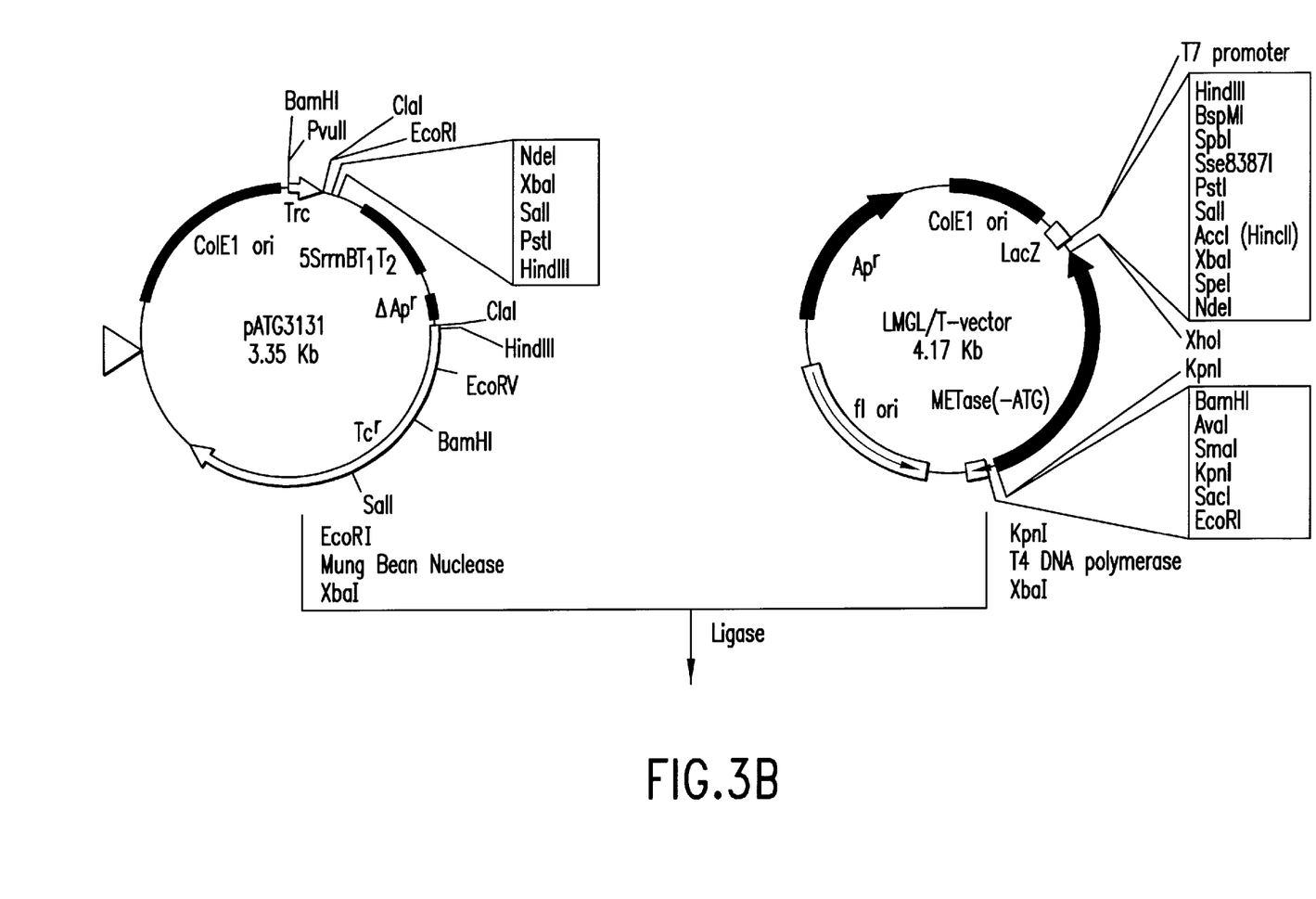
Figure 3C:
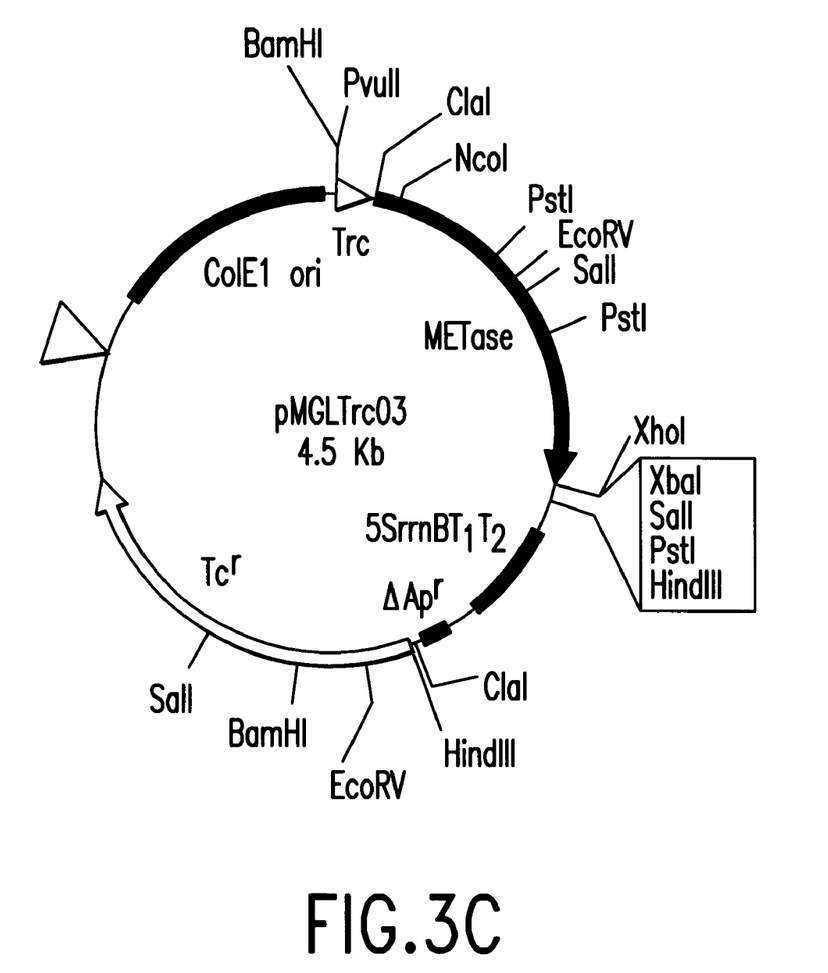

Next, rMETase(-ATG) of LMGL/T-vector was inserted in downstream of the initiation codon of plasmid pATG3131 which contained trc promoter, SD sequence, initiation codon (ATG), 5SrrnBT$_1$T$_2$ terminator and tetracycline resistant gene. At first, 5 μg of pATG3131 was digested with restriction enzyme EcoRI, flushed by Mung Bean Nuclease and digested with restriction enzyme XbaI, followed by electrophoresis on an agarose gel to recover 3.3 kbp of fragments by SpinBind. On the other hand, 10 μg of LMGL/T-vector was digested with restriction enzyme KpnI, flushed by a DNA Blunting kit (Takara Shuzo Co.) and digested with restriction enzyme XbaI, followed by electrophoresis on an agarose gel to recover 1.2 kbp of fragments. These two fragments were added to Ready-To-Go™ T4 DNA ligation kit and incubated at 16° C. for 45 minutes, and then E.coli JM 109 was transformed. This transformant was incubated on an agar medium containing tetracycline, from which a plasmid containing the objective gene was selected and named as pMGLTrc03 (FIG. 3).

Example 5
Preparation of rMETase Crystals—(3)

rMETase expression strain was prepared by introducing rMETase expression plasmid pMGLTrc03 into E.coli JM 109. The obtained strain was grown in LB as a preseed medium and further in LB containing 0.5% glucose as a seed medium, then cells were cultured in Terrific broth (Funakoshi) containing 4% glycerol at 28° C. for 24 hours by three 30-l jar fermentors. 57 kg of the obtained culture broth was centrifuged (Alfa Laval) to collect 19 kg of concentrated cells, to which was added 17.4 kg of 100 mM Na-PB solution (pH 7.5) containing 24.57 g EDTA, 10.34 g PLP and 3.3 g DTT. The obtained suspension of cells was heated at 28° C. and subjected to a high pressure homogenizer (APV-Gaulin) to disrupt. The temperature after the disruption was 42° C. 2.18 L of 5% Kurimover I solution was added to 36.6 kg of the obtained solution within about 5 minutes and the mixture was stirred for 20 minutes. 38.8 kg of the resultant solution was centrifuged to give 37.4 kg of a crude enzyme solution. The obtained solution contained 160 g of rMETase whose specific activity was 30 U/mg.

8.86 kg of ammonium sulfate was gradually added to the crude enzyme solution (40% saturation). The solution was adjusted by aqueous ammonia to be pH 7.2 for dissolving ammonium sulfate. The enzyme was precipitated by salting and stored in a refrigerator. The precipitates were collected by a centrifugal separator (Sharples). The precipitates were dissolved into 3.6L of a dissolution buffer (0.5 mM PLP, 0.05% 2-ME, 20 mM Na-PB, pH7.2), to which was added a solution of 150 g of ammonium sulfate dissolved in 0.2 L of the dissolution buffer. This solution was adjusted by aqueous ammonium to be pH 7.2 and cooled to 4° C., to which was added 1.6 L of a dissolution buffer containing 540 g of PEG 6,000 gradually, and the mixture was stirred at 4° C. for 60 minutes. After eliminating insoluble substances by centrifugation, 5.4 L of the dissolution buffer containing 650 g of PEG 6,000 was gradually added with stirring, and the resultant mixture was warmed to 32° C., then 540 ml of 4 M NaCl solution was added with stirring for 20 minutes. Further stirring at 32° C. for 60 minutes produced prismatic crystals of rMETase. Further stirring at 4° C. for 20 hours for growing the crystals and centrifugation gave the prismatic crystals of rMETase.

Example 6
Preparation of rMETase Crystals—(4)

The prismatic crystals obtained above were dissolved in 6 L of the dissolution buffer, from which insoluble substances were eliminated by centrifugation, then 2.4 L of the dissolution buffer containing 760 g of PEG 6,000 was gradually added thereto and the resultant mixture was warmed to 32° C. 420 ml of 4 M NaCl solution was added for 20 minutes with stirring and the mixture was stirred at 32° C. for 60 minutes. Further stirring at 4° C. for 20 hours produced the bi-pyramidal crystals of rMETase, which were collected by centrifugation and dissolved in 6 L of the dissolution buffer. 125 g of rMETase was contained in 6.3 L of the obtained crystal-redissolution buffer and the specific activity was 50 U/mg.

Example 7
Purification of rMETase With Column Chromatography After Crystallization—(2)

The crystal-redissolution solution obtained in Example 6 was subjected to DEAE-Sepharose FF (Amersham Pharmacia Biotech.) column chromatography which had been equilibrated with 20 mM Na-PB (pH 7.2). The column was washed with 20 mM Na-PB (pH 7.2) containing 0.1 mM PLP and 0.01% 2-ME. The enzyme was eluted with 20 mM Na-PB (pH 7.2) containing 120 mM NaCl, 0.1 mM PLP and 0.01% 2-ME. Its specific activity was 52 U/mg. 15 L of the obtained active fraction was concentrated to 2.7 L by a membrane which has a cutting size of 100 kDa (Millipore). The concentrated solution contained 101 g of rMETase. 900 ml of the concentrated solution was subjected to 18 L of Sephacryl S-200 HR (Amersham Pharmacia Biotech) column chromatography equilibrated with 10 mM Na-PB (pH 7.2) containing 0.01 min PLP. This operation was performed three times. The obtained effective active fraction contained 80 g of rMETase of which specific activity was 52 U/mg.

The specific activity and yield of rMETase after each operation in Examples 5 to 7 were shown in Table 3.

TABLE 3

| | | Kurimover I Treatment | |
|---|---|---|---|
| | Purification Step | Sp. act. (U/mg) | yield (%) |
| Example 5 | Supernatant after cell disruption | 24 | 100 |
| | Crude enzyme solution | 25 | 99 |
| | Unpurified rMETase solution | 40 | 89 |
| | rMETase prismatic crystals | 52 | 80 |
| Example 6 | rMETase bi-pyramidal crystals | 52 | 77 |
| Example 7 | DEAE-Sepharose FF | 52 | 64 |
| | Concentrated solution | 52 | 62 |
| | Sephacryl S-200 HR | 52 | 50 |

Sp. act: Specific Activity

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: sense PCR primer

<400> SEQUENCE: 1
cccggtacca cggctccaac aagctcccag                30

<210> SEQ ID NO 2
<211> LENGTH: 27
<212> TYPE: DNA
<213> ORGANISM: Artificial Sequence
<220> FEATURE:
<223> OTHER INFORMATION: antisense PCR primer

<400> SEQUENCE: 2
ctcgagacgg gttcaggcac tcgcctt                27

INDUSTRIAL APPLICABILITY

A method for producing L-methionine γ-lyase crystals of the present invention can purify L-methionine γ-lyase to the same or higher level than that obtained by column chromatography. The purification method using crystallization provides the pure objective compound economically and on a large scale as compared to chromatography. Therefore, the method for producing the crystals of the present invention is useful as an industrial purification of L-methionine γ-lyase.

What is claimed is:

1. process for producing L-methionine γ-lyase crystals which comprises dissolving precipitate containing L-methionine γ-lyase in a buffered solution at a temperature in the range of about 2° C. to about 15° C. to form a solution containing L-methionine γ-lyase, adding polyethylene glycol to the solution and warming the solution to a temperature in the range of about 25° C. to about 40° C., and adding an inorganic salt to the warm solution to promote formation of L-methionine γ-lyase crystals.

2. The process of claim 1, wherein said inorganic salt is sodium chloride or potassium chloride.

3. The process of claim 1, wherein the final concentration of the inorganic salt is from about 20 mM to about 500 mM.

4. The process of claim 1, wherein said polyethylene glycol has an average molecular weight of not less than about 7,200.

5. The process of claim 1, wherein the final concentration of polyethylene glycol is from about 5% (W/V) to about 25% (W/V).

6. The process of claim 1, wherein warming is performed before addition of polyethylene glycol to the L-methionine γ-lyase solution.

7. The process of claim 1, wherein warming is performed after addition of polyethylene glycol to the L-methionine γ-lyase solution.

8. The process of claim 1, wherein addition of polyethylene glycol to the L-methionine γ-lyase solution is performed before and after warming.

9. The process of claim 1, which comprises a step of eliminating impurities after addition of polyethylene glycol to the L-methionine γ-lyase solution and before warming thereof.

10. The process of claim 9, wherein said elimination is performed by adding polyethylene glycol in the presence of ammonium sulfate.

11. The process of claim 1, wherein the concentration of L-methionine γ-lyase in the L-methionine γ-lyase-containing solution is from about 4 g/L to about 30 g/L.

12. The process of claim 1, wherein the L-methionine γ-lyase-containing solution is treated with a cationic high molecular weight coagulant.

13. The process of claim 12, wherein said cationic high molecular weight coagulant is polyethyleneimine.

14. The process of claim 12, wherein the main component of the cationic high molecular weight coagulant is chitosan.

15. The process of claim 12, wherein said cationic high molecular weight coagulant is Kurimover I.

16. The process of claim 1, wherein a series of steps, of redissolution of L-methionine γ-lyase, warming the solution before or after addition of or to polyethylene glycol, and adding an inorganic salt, are repeated one or more times.

17. The process of claim 1, wherein column chromatography is performed after the process as claimed.

18. A crystal of recombinant L-methionine γ-lyase which is produced by the process as claimed in claim 1.

19. The process of claim 16, wherein column chromatography is performed after the process as claimed.

20. A crystal of recombinant L-methionine γ-lyase which is produced by the process as claimed in claim 16.

* * * * *